United States Patent
Spivak et al.

(10) Patent No.: US 6,696,549 B1
(45) Date of Patent: Feb. 24, 2004

(54) ANTIBODIES TO THE CYTOPLASMIC DOMAIN OF THE THROMBOPOIETIN RECEPTOR

(75) Inventors: Jerry Spivak, Baltimore, MD (US); Alison Moliterno, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 92 days.

(21) Appl. No.: 09/652,037

(22) Filed: Aug. 31, 2000

Related U.S. Application Data

(62) Division of application No. 09/081,618, filed on May 20, 1998, now Pat. No. 6,150,120.
(60) Provisional application No. 60/047,216, filed on May 20, 1997.

(51) Int. Cl.[7] .............................................. C07K 16/28
(52) U.S. Cl. .............................. 530/388.22; 530/387.9; 530/388.1; 530/351
(58) Field of Search .............................. 530/350, 351, 530/387.9, 388.1, 388.22

(56) References Cited

PUBLICATIONS

Y. Li et al. "Proto–oncogene c–mpl is involved in spontaneous megakaryocytopoiesis in myeloproliferative disorders" British Journal of Haematology 92 (1) 1996.
Alison R. Moliterno et al. "Impaired Expression of the Thromboprotein Receptor by Platelets from Patients with Polycythemia Vera" The New England Journal of Medicine 338:572–580 (Feb. 26, 1998).
Isabelle Vigon et al. "Molecular cloning and characterization of MPL, the human homolog of the v–mpl oncogene: Identification of a member of the hematopoietic growth factor receptor superfamily" Proc. Natl. Acad. Sci. USA vol. 89 pp. 5640–5644 Jun. 1992.
Vicent Mignotte et al. "Structure and Transcription of the Human c–mpl Gene (MPL)" Genomics 20, 5–12 (1994).
A. Moliterno et al. "thromboprotein Fails to Stimulate Protein Tyrosine Phosphorylation in Polycthemia Vera Platelets" Blood 88 (Suppl. 1); 1996; p640Aa, Abstract No. 2547 (10 Suppl. 1 Part 1–2).

A. Moliterno et al; "Loss of Thromboprotein Signal Transduction and Membrane Receptor, Mpl, is associated with Polycythemia Vera and Idiopatheic Myelofibrosis" Blood 90 (Suppl. 1); 1997; p346a, Abstract No. 1544.
Alison R. Moliterno et al.; "A Novel Thrombopoietin Signaling Defect in Polycythemia Vera Platelets" Stem Cells 1998; 16 (suppl 2): p185–192.
A. Cerutti et al., Brit. J. Haematol. 99:281–294, 1997.
J.G. Drachman et al., "The c–Mpl ligand (thrombopoietin) stimulates tyrosine phosphorylation of Jak2, Shc, and c–Mpl", J. Biological Chemistry 270(10):4979–4982, 1995.*
L. Beguinot et al., "Functional studies on the EGF receptor with an antibody that recognizes the intracellular portion of the receptor", J. Biological Chemistry 261(4):1801–1807, 1986.*
K. Miyaji et al., "Effect of tyrphostin on cell growth an dtyrosinetyrosine kinase activity of epidermal growth factor receptor in human gliomas", J. Neurosurg., 81:411–419, 1994.*

* cited by examiner

*Primary Examiner*—Lorraine Spector
(74) *Attorney, Agent, or Firm*—Banner & Witcoff, Ltd.

(57) ABSTRACT

Impaired TPO-mediated platelet protein tyrosine phosphorylation was consistently observed in patients with polycythemia vera (PV) as well as those with idiopathic myelofibrosis (IMF), in contrast to patients with essential thrombocytosis, chronic myelogenous leukemia, secondary erythrocytosis, iron deficiency anemia, hemochromatosis or normal volunteers. Moreover, the platelet TPO receptor, Mpl, was not detectable by immunoblotting with an antibody to the extracellular domain, by chemical crosslinking of TPO to the surface of platelets, or by flow cytometry using an antibody to the extracellular domain, in 34 of 34 PV patients and also in 13 of 14 IMF patients. Impaired TPO-induced protein tyrosine phosphorylation in PV and IMF platelets was uniformly associated with markedly reduced or absent expression of the extracellular domain of Mpl. Thus the reduced detectablility of Mpl by these methods can be used a marker of PV and IMF. The abnormality appears to distinguish PV from other forms of erythrocytosis and may be involved in the platelet function defect associated with PV.

3 Claims, 9 Drawing Sheets

(1 of 9 Drawing Sheet(s) Filed in Color)

1 2 3 4

[Γ-³²P]-ATP
INCORPORATION

JAK2

ANTIBODIES TO THE CYTOPLASMIC DOMAIN OF THE THROMBOPOIETIN RECEPTOR

This application is a divisional of U.S. Ser. No. 09/081,618, filed May 20, 1998, now U.S. Pat. No. 6,150,120, which claims the benefit of provisional application Ser. No. 60/047,216, filed May 20, 1997.

This invention was made employing funds from an N.I.H. Institutional NSRA (NHLBI) grant HL 75025. The government therefore retains certain rights in the invention.

BACKGROUND OF THE INVENTION

Polycythemia vera (PV), idiopathic myelofibrosis (IMF), chronic myelogenous leukemia (CML) and essential thrombocythemia (ET) are classified as the chronic myeloproliferative disorders because their pathophysiology involves the clonal expansion of a multipotent hematopoietic progenitor cell with the over-production of one or more of the formed elements of the blood (1,2,3,4). However, with the exception of CML, these disorders lack a clonal marker, their pathogenesis is unknown, and their diagnosis therefore is dependent upon clinical criteria. Remarkably, in spite of their origin from a transformed clone, the mature circulating blood cells in these disorders are morphologically normal and, in contrast to CML, progression to acute leukemia is far less common in PV, ET and IMF. Furthermore, while these latter disorders can mimic each other clinically, they have distinctly different clinical courses and differ with respect to their treatment. Therefore, the identification of a diagnostic marker would be very useful.

Polycythemia vera is the commonest of the chronic myeloproliferative disorders and although its hallmark is trilineage hyperplasia, erythrocytosis is its most prominent clinical manifestation. For this reason, most investigators have focused on erythropoiesis in PV in an attempt to define its etiology but without notable success. There is a need in the art for diagnostic methods for distinguishing PV from other diseases involving erythrocytosis.

SUMMARY OF TIE INVENTION

It is an object of the invention to provide methods of distinguishing polycythemia vera and idiopathic myelofibrosis from other diseases causing erythrocytosis.

It is another object of the invention to provide a method to aid in the diagnosis of polycythemia vera.

It is yet another object of the invention to provide an antibody useful in the diagnosis of polycythemia vera.

These and other objects of the invention are provided by one or more of the embodiments; described below.

In one embodiment a method is provided for distinguishing polycythemia vera and idiopathic myelofibrosis from other diseases causing erythrocytosis. The method comprises the steps of: contacting platelets or megakaryocytes of a patient with thrombopoietin; and determining whether the step of contacting with thrombopoietin causes proteins of the platelets or megakaryocytes to become phosphorylated on tyrosine residues; wherein a patient is identified as having polycythemia vera or idiopathic myelofibrosis when the step of contacting with thrombopoietin does not cause phosphorylation on tyrosine residues of platelet proteins, or wherein a patient is identified as not having polycythemia vera or idiopathic myelofibrosis when the step of contacting with thrombopoietin does cause phosphorylation on tyrosine residues of platelet proteins.

In another embodiment a method is provided to aid in the diagnosis of polycythemia vera. The method comprises the steps of: measuring thrombopoietin level of a blood sample isolated from a patient suspected of having polycythemia vera or idiopathic myelofibrosis; and comparing the measured level of thrombopoietin to the levels of thrombopoietin of a population of normal human controls; wherein a patient is identified as potentially having polycythemia vera or idiopathic myelofibrosis if the measured thrombopoietin level is more than two standard deviations above the mean value of the population.

In still another embodiment of the invention another method is provided for distinguishing polycythemia vera and idiopathic myelofibrosis from other diseases causing erythrocytosis. The method comprises the step of testing the ability of Mpl of platelets or megakaryocytes isolated from a patient suspected of having erythrocytosis to bind to thrombopoietin, wherein an Mpl which has diminished ability to bind thrombopoietin compared to wild-type Mpl indicates that the patient has polycythemia vera or idiopathic myelofibrosis, and wherein an undiminished ability to bind thrombopoietin compared to wild-type Mpl indicates that the patient does not have polycythemia vera or idiopathic myelofibrosis.

In yet another embodiment of the invention a method is provided for distinguishing polycythemia vera and idiopathic myelofibrosis from other diseases causing erythrocytosis. The method comprises the step of: determining the presence or absence of a wild-type Mpl in platelets or megakaryocytes isolated from a patient by subjecting proteins isolated from the platelets or megakaryocytes to two-dimensional gel electrophoresis, wherein an altered isoelectric focusing point of Mpl indicates that the patient has polycythemia vera or idiopathic myelofibrosis.

In another embodiment of the invention another method of distinguishing polycythemia vera and idiopathic myelofibrosis from other diseases causing erythrocytosis is provided. The method comprises the step of: determining the presence or absence of a wild-type Mpl in platelets or megakaryocytes isolated from a patient by subjecting proteins isolated from the platelets or megakaryocytes to isoelectric focusing gel electrophoresis, wherein an altered isoelectric focusing point of Mpl indicates that the patient has polycythemia vera or idiopathic myelofibrosis.

In yet another embodiment of the invention a method of distinguishing polycythemia vera and idiopathic myelofibrosis from other diseases causing erythrocytosis is provided. The method comprises the steps of: contacting platelets of a patient with thrombopoietin; and determining whether the step of contacting with thrombopoietin potentiates aggregation of the platelets; wherein a patient is identified as having polycythemia vera or idiopathic myelofibrosis when the step of contacting with thrombopoietin does not potentiate aggregation of platelets, or wherein a patient is identified as not having polycythemia vera or idiopathic myelofibrosis when the step of contacting with thrombopoietin does potentiate aggregation of platelets.

In still another embodiment of the invention an antibody preparation is provided. The antibody preparation specifically binds to the cytoplasmic domain of Mpl protein and does not specifically bind to the extracellular domain of Mpl.

In another embodiment of the invention a method is provided for distinguishing polycythemia vera and idiopathic myelofibrosis from other diseases causing erythrocytosis. The method comprises the steps of: determining in platelets or megakaryocytes isolated from a patient, subcellular localization of Mpl, a receptor for thrombopoietin, wherein a membrane bound form of Mpl indicates that the patient does not have polycythemia vera or idiopathic myelofibrosis, and wherein a cytosolic form of Mpl indicates that the patient has polycythemia vera or idiopathic myelofibrosis.

According to still another embodiment of the invention a method of distinguishing polycythemia vera and idiopathic myelofibrosis from other diseases causing erythrocytosis is provided. The method comprises the steps of: isolating nucleic acids from hematopoietic cells of a patient; and determining whether the nucleic acids encode a wild-type or mutant extracellular domain of Mpl, a thrombopoietin receptor, wherein a mutant extracellular domain of Mpl indicates that the patient has polycythemia vera or idiopathic myelofibrosis, and wherein a wild-type extracellular domain of Mpl indicates that the patient does not have polycythemia vera or idiopathic myelofibrosis.

In another aspect of the invention a method is provided for distinguishing polycythemia vera and idiopathic myelofibrosis from other diseases causing erythrocytosis. The method comprises the step of: utilizing an antibody which binds to the wild-type extracellular domain of Mpl, a thrombopoietin receptor, to determine the presence or absence of the wild-type extracellular domain of Mpl in platelets or megakaryocytes isolated from a patient suspected of having erythrocytosis, wherein the presence of the wild-type extracellular domain indicates that the patient does not have polycythemia vera or idiopathic myelofibrosis, and the absence of the wild-type extracellular domain indicates that the patient does have polycythemia vera or idiopathic myelofibrosis.

These and other embodiments of the invention provide the art with reagents and methods for specifically and simply distinguishing polycythemia vera from other diseases associated with erythrocytosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Impaired TPO-induced protein tyrosine phosphorylation in PV platelets.

FIG. 3. Markedly reduced PV platelet Mpl expression.

DETAILED DESCRIPTION OF THE PREFERRED EMBODIMENTS

Figure 1A:
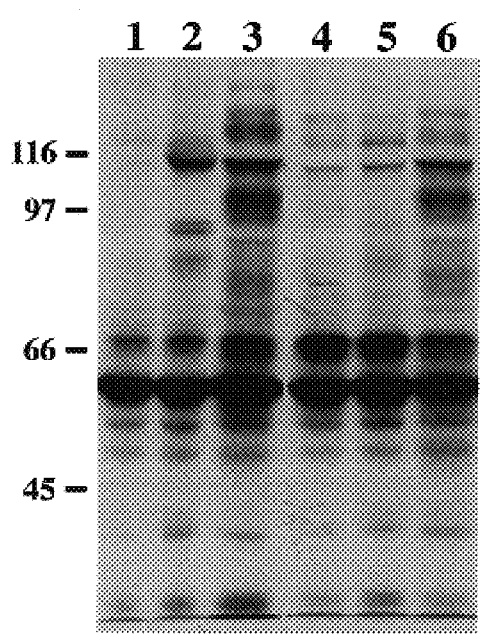
FIG. 1A) Phosphotyrosine immunoblot of platelet lysates from normal (lanes 1, 2 and 3) or PV patients (lanes 4, 5 and 6). Platelets were unstimulated (lanes 1 and 4), stimulated with TPO (100 ng/ml for 10 minutes at room temperature) (lanes 2 and 5), or thrombin (2 units/ml for 2 minutes at room temperature) (lanes 3 and 6).

It is a discovery of the present inventors that polycythemia vera (PV) and idiopathic myelofibrosis (IMF) but not essential thrombocythemia (ET) or chronic myelogenus leukemia (CML) platelets have aberrant expression of Mpl, the thrombopoietin receptor. This defect can be exploited to distinguish PV and IMF from amongst the chronic myeloproliferative disorders and from other disorders causing erythrocytosis.

The Mpl receptor has been cloned and sequenced and is reported in the literature (6, 7). The sequences have been deposited in the Gen Bank data base as accession nos.

M90102 and M90103, as well as in the EMBL Data Library under Accession Nos. X73551 and X73552. These sequences are expressly incorporated by reference herein While these papers report a P and K form of the receptor, in our hands only the P form has been observed.

While aberrant patterns of protein expression have been observed, the mRNA for Mpl has been observed at normal levels in PV platelets. We have determined that the defect in Mpl appears to be localized in the ligand binding domain of the extracellular domain of the protein. The cytoplasmic domain of Mpl is detected normally in PV platelets. The difference between normal and the PV form of Mpl can be observed in either two-dimensional electrophoresis or by isoelectric focusing. The PV form of the protein has an altered isoelectric point. Moreover, the altered form of Mpl does not bind its ligand, TPO. In addition, it appears that the altered form of Mpl is not processed correctly, as it is aberrantly localized in the cell in the cytosolic fraction, rather than in the particulate fraction.

These observations of the abnormal Mpl found in PV platelets, coupled with the strong association of the abnormal Mpl in PV and IM, permit a number of diagnostic tests to be used to distinguish polycythemia vera and idiopathic myelofibrosis from other diseases causing erythrocytosis.

Since Mpl is expressed in both platelets and megakaryocytes, either can be used as a diagnostic sample. Platelets are easier to obtain as they are found in the peripheral blood, while megakaryocytes are mainly confined to the bone marrow. Techniques for obtaining these cells are well known to hematologists.

Since PV Mpl is thrombopoietin insensitive, platelets and megakaryocytes can be contacted with thrombopoietin and then the proteins can be analyzed to see if they become phosphorylated on tyrosine residues. In normal cells TP stimulates such phosphorylation. Phosphorylation can be observed using any technique known in the art. These include, but are not limited to, use of an antiphosphotyrosine antibody, or incubation with radiolabeled phosphate and detection with an antibody specific for a phosphotyrosine substrate, such as JAK2, STAT5, and TYK2.

Because TPO is not bound by Mpl in PV patients, it is not further metabolized as it is in normal cells. Thus, it appears that TPO accumulates in platelets and megakaryocytes of PV patients. The thrombopoietin level of a blood sample isolated from a patient suspected of having polycythemia vera or idiopathic myelofibrosis can thus be determined. The sample can be a plasma sample, preferably which has been treated with EDTA. Any technique known in the art can be used for detecting TPO, including, but not limited to an enzyme-linked immunoassay. The measured level of thrombopoietin in the blood sample is compared to the levels of thrombopoietin of a population of normal human controls. The levels of TPO in the population vary quite a lot, and can be affected by many different factors. If the level determined is more than two standard deviations above the mean value of the population, then an abnormality is suggested which may be polycythemia vera or idiopathic myelofibrosis.

As mentioned above, Mpl in PV patients does not bind to TPO. Thus TPO binding can be used as a diagnostic assay for PV. Mpl of platelets or megakaryocytes isolated from a patient suspected of having erythrocytosis can be tested for the ability to bind to thrombopoietin. The Mpl may be isolated from the cells, or whole cells can be used. Finding an Mpl which has diminished ability to bind thrombopoietin compared to wild-type Mpl indicates that the patient has polycythemia vera or idiopathic myelofibrosis. Finding an undiminished ability to bind thrombopoietin compared to wild-type Mpl indicates that the patient does not have polycythemia vera or idiopathic myelofibrosis.

The Mpl found in PV platelets and megakaryocytes appears very similar to wild-type Mpl found in normal blood when viewed on polyacrylamide gel electropherograms. However, using the classic techniques of two-dimensional gel electrophoresis or isoelectric focusing, differences are detectable between Mpl in PV and normal patients. The altered mobility in these two types of electropherograms reflects an altered isoelectric focusing point. After subjecting proteins from the platelets or megakaryocytes to electrophoresis, the proteins can be visualized by blotting and immunoreacting with an antibody to the cytoplasmic domain of Mpl. Alternatively, the proteins can be immunoprecipitated prior to electrophoresis and subsequently stained with a standard protein stain. Even in one-dimensional gel electrophoresis a difference can be observed between normal and PV Mpl. If the proteins are blotted and stained with an antibody to the cytoplasmic domain of Mpl, one can see two forms of the protein at approximately 85 and 82 KD in normal samples, but only one 82 KD protein in PV samples. This too can be used diagnostically.

In normal cells TPO potentiates thrombin-mediated platelet aggregation. However, the variant of Mpl found in PV is insensitive to TPO. Thus, it has been found that TPO fails to potentiate the aggregation of platelets in PV samples. Potentiation can be measured as an increased rate, or as a lowering of the amount of thrombin required to achieve the same result. Aggregation can be monitored using standard techniques known in the art. Typically the aggregation studies are done in whole blood samples. Monitoring of the aggregation typically employs an optical reader which measures light transmission, light diffraction, or light absorbance. Aggregometers which can be used can be obtained from Chrono-Log, Broomall, Pa. 19008; Payton Associates, Buffalo, N.Y. 14202, and Bio-Data Corporation, Hatboro, Pa. 19040.

Antibodies have been found which are able to detect both normal and aberrant Mpl found in PV. The antibodies specifically bind to the cytoplasmic domain of Mpl protein and do not specifically bind to the extracellular domain of Mpl. Such antibodies can be polyclonal or monoclonal. Techniques for making either type of antibody preparations are well known in the art. An immunogen for making such antibodies can be a fusion protein comprising only the cytoplasmic domain of Mpl, or can be a peptide portion of Mpl representing only a portion of the cytoplasmic domain of Mpl.

As mentioned above, the Mpl found in PV platelets and megakaryocytes appears to be aberrantly post-translationally processed. This appears to lead to the failure to be inserted into the cell membrane. Thus if one fractionates platelets or megakaryocytes into a particulate (membrane) and a soluble (cytoplasmic) fraction, and analyzes the fractions for Mpl, one finds Mpl in the particulate fraction in normal patients, but in the cytoplasmic fraction in PV or idiopathic myelofibrosis. This can be used to provide a diagnosis or to aid in diagnosis.

The aberrant Mpl found in platelets and megakaryocytes is caused by a mutation in Mpl. Such mutations can be detected and used diagnostically. Nucleic acids can be isolated from hematopoietic cells of a patient. The hematopoietic cells are preferably bone marrow cells, white blood cells, peripheral blood cells, or platelets. RNA can be isolated from platelets or megakaryocytes and DNA can be isolated from megakaryocytes, for example. Any means known in the art can be used to analyze the nucleic acids for mutations, including but not limited to determining the nucleotide sequence, hybridizing with oligonucleotide probes which detect the coding region for the extracellular domain of Mpl, amplifying the region encoding the extracellular domain of Mpl, and analyzing the structure of the RNA for Mpl. Preferably the part of the nucleic acids encoding the ligand binding domain of Mpl is determined. More preferably the sequence of exon 2 is determined. Patient samples can be compared to bona fide normal or wild-type samples.

It has been found that an antibody which binds to the wild-type extracellular domain of Mpl, a thrombopoietin receptor, is particularly useful for distinguishing between wild-type and PV Mpl. Such an antibody immunoreacts with wild-type extracellular domain of Mpl in platelets or megakaryocytes but does not immunoreact with Mpl found in PV and idiopathic myelofibrosis. One such antibody is an affinity purified, polyclonal rabbit IgG antibody to the soluble extracellular domain of human Mpl, which was; obtained from Kirin Brewery, Maebashi, Gunma, Japan. Other such antibodies can be made using, for example the 463 amino acids of the extracellular domain as an immunogen to raise antibodies. If the antibodies to the extracellular domain do not detect an Mpl, a second antibody staining may be desired to confirm that Mpl is present, albeit aberrantly. A suitable antibody for such purpose is one which binds to an epitope within the intracellular domain of Mpl.

Immunological techniques which can be used according to the present invention include immunoblots, flowcytometric analysis, immunoprecipitation, and immunohistochemical staining. Others which are known in the art can also be used.

The chronic myeloproliferative disorders, PV, IMF, and ET, share in common an origin in a multipotent hematopoietic progenitor cell and an increase in the number of one or more of the formed elements of the blood. Although clonal in nature, clonal markers have not been previously identified for PV, IMF or ET nor is their pathogenesis understood. Furthermore, since PV can present initially with an isolated leukocytosis, thrombocytosis or even myelofibrosis and myeloid metaplasia or eventually evolve into the latter, it can be difficult to distinguish amongst PV, IMF and ET clinically. This is not a trivial consideration since the natural history, treatment and prognosis of PV,IMF and ET differ (8).

A number of experimental and clinical studies have failed to implicate the erythropoietin receptor in the pathogenesis of PV (9–11). We examined Mpl-mediated platelet protein tyrosine phosphorylation following exposure to TPO in vitro. Mpl is a member of the hematopoietic growth factor receptor superfamily and like the other hematopoietic growth factor receptors, binding of its cognate ligand causes Mpl oligomerization and activation of members of the Janus family of tyrosine kinases, in particular JAK2 and Tyk2. Activation of these kinases is associated with tyrosine phosphorylation of a number of proteins including members of the STAT family (in platelets, STAT3 and STAT5 specifically) and Shc (12, 13). To our surprise, exposure of PV platelets to TPO failed to activate JAK2 or Tyk2 and as a consequence neither STAT5 nor Shc were tyrosine phosphorylated even though these kinases and their substrates were expressed normally in PV platelets and thrombin-induced protein tyrosine phosphorylation was intact. In contrast to CML, in which growth factor-independent platelet protein tyrosine phosphorylation occurs as a consequence of the constitutively-active kinase, bcr-abl, we found no constitutive tyrosine phosphorylation of PV platelet proteins.

The biologic basis for this abnormality in TPO-mediated protein tyrosine phosphorylation in PV platelets appeared to be diminished expression of platelet Mpl. Diminished expression of platelet prostaglandin D2 receptors in some patients with chronic myeloproliferative disorders and α-adrenergic receptors in the platelets of some ET patients provide an interesting parallel to our observations (14,15). However, the remarkable consistency of reduced Mpl in PV platelets is novel and cannot be explained by accelerated proteolytic degradation of Mpl or TPO-induced receptor down regulation. It is also of interest that the 13 of 14 IMF patients whom we have examined expressed a similar defect in platelet Mpl expression. This suggests a close relationship between PV and IMF, a contention which is strengthened by the clinical conversion between PV and IMF. Importantly, amongst patients with erythrocytosis, altered Mpl expression was specific for PV as defined by the currently accepted clinical criteria (8) and could not be explained as a consequence of iron deficiency, splenomegaly, prior therapy including periodic phlebotomy, disease duration or a hyperactive bone marrow.

Our results indicate loss of receptor immunologic identity and function. The uniformity of expression of this abnormality in PV platelets suggests that it is intimately connected with the disease process. Whether abnormal Mpl expression represents a late consequence of the abnormality causing PV or an obligatory early event, this abnormality provides a new avenue for investigation of the pathogenesis of this disease and its associated defective platelet function, as well as a marker to distinguish PV from other causes of erythrocytosis.

The following examples are not intended to limit the scope of the invention, but merely to exemplify that which is taught above.

EXAMPLES

Example 1

This example describes platelet protein tyrosine phosphorylation.

To assess TPO signaling in platelets, we stimulated washed platelets with TPO or thrombin, and then assessed protein tyrosine phosphorylation by immunoblotting. As shown in FIG. 1A, following exposure of normal platelets to a saturating concentration of TPO (100 ng/ml for 10 minutes), proteins with apparent molecular masses of 125, 95 and 85 kDa were tyrosine phosphorylated. By contrast, exposure of PV platelets to a comparable concentration of TPO failed to induce significant protein tyrosine phosphorylation. This was not a consequence of a global impairment of platelet tyrosine phosphorylation, since thrombin induced a similar pattern of protein tyrosine phosphorylation in both normal and PV platelets. Neither increasing the concentration of TPO nor the duration of exposure (1000 ng/ml for up to 30 minutes) induced significant protein tyrosine phosphorylation in PV platelets (data not shown).

Figure 1B:
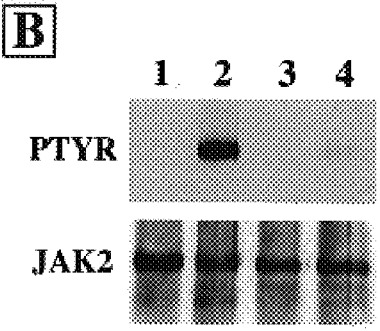
FIG. 1B) Anti-phosphotyrosine immunoblot of JAK2 immunoprecipitates from normal (lanes 1 and 2) and PV lanes 3 and 4) platelet lysates (upper panel). Platelets were either unstimulated lanes 1 and 3) or stimulated with TPO lanes 2 and 4). The membrane was then stripped and reprobed with JAK2 antiserum to demonstrate equal protein loading lower panel).
Figure 1C:
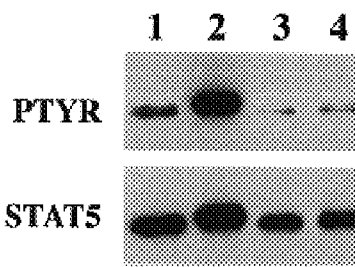
FIG. 1C) Anti-phosphotyrosine immunoblot of STAT5 immunoprecipitates from normal (1,2) and PV (3,4) platelet lysates, unstimulated (lanes 1 and 3), and after TPO stimulation lanes 2 and 4). The membrane was reprobed with STAT5 antiserum lower panel).

To examine more closely TPO-induced tyrosine phosphorylation, we evaluated the well characterized members of the Mpl signaling cascade in platelets, JAK2 and its substrate, STAT5 (12,13). To determine if JAK2 was functionally intact in PV platelets, we examined its tyrosine phosphorylation following TPO exposure. As shown in FIG. 1B, TPO-induced JAK2 tyrosine phosphorylation was impaired in PV platelets even though by immunoblotting the quantity of JAK2 protein present was comparable in PV and normal platelets. Similarly, TPO-induced tyrosine phosphorylation of STAT5 was impaired in PV platelets, despite the presence of equivalent quantities of STAT5 in normal and PV platelets FIG. 1C). As might be expected, TYK2 and Shc tyrosine phosphorylation were also impaired in PV platelets following TPO exposure in contrast to normal platelets (data not shown). The results of these studies suggested that the diminished JAK2 and STAT5 responses in PV platelets were due to an upstream defect in JAK2, Mpl, or other components of the TPO signaling pathway. In this regard, interleukin 11 had no effect on tyrosine phosphorylation in either normal or PV platelets (data not shown).

Methods

Subjects. We studied 64 patients with chronic myeloproliferative disorders: 34 with PV, 14 with IMF, 9 with ET and 7 with CML. The study protocol was approved by our Joint Committee on Clinical Investigation and informed consent was obtained from each patient. The diagnosis of PV was based on the recommendations of the Polycythemia Vera Study Group (PVSG) (16) including demonstration of an elevated red cell mass, while that of the other chronic myeloproliferative disorders was based on standard published clinical criteria (8). Control subjects included 14 patients with erythrocytosis (2 post renal transplant, 1 with congenital heart disease, 1 with a hemoglobin variant, and 10 of unknown cause), 8 with hemochromatosis who were undergoing periodic therapeutic phlebotomy, 2 patients with uncomplicated iron deficiency and 10 normal volunteers (Table 1).

Platelet Protein Tyrosine Phosphorylation. Venous blood collected in 3.8% sodium citrate was centrifuged at 160 g for ten minutes to obtain platelet rich plasma (PRP). The PRP was spun at 750 g for 12 minutes and the platelet pellet was washed three times with phosphate-buffered saline containing 0.5% bovine serum albumin and 0.6% sodium citrate (wash buffer). The platelets were resuspended in the wash buffer, enumerated in an electronic particle counter, and the volume of buffer adjusted to yield a platelet concentration of $10^9$/ml. Platelets were exposed to thrombin or TPO at selected concentrations for the indicated time periods at room temperature and then lysed in 20 mM Tris pH 7.5 containing 1% NP40, 137 mM NaCl, 10% glycerol, 1 mM EDTA, 50 mM NaF, 5 mM $MgCl_2$, 2 mM sodium vanadate, 1 mM PMSF, 2 µg/ml aprotinin, 2 µg/ml leupeptin, and 1µg/ml pepstatin (lysis buffer). The protein concentration of the platelet lysates was quantitated by the bicinchoninic acid technique.

Immunoblotting and Immunoprecipitation of Platelet Lysates. Equal aliquots of platelet lysate protein were subjected to SDS-7.5% polyacrylamide gel electrophoresis (SDS-PAGE) and transferred to a nitrocellulose membrane at 20 V for 16 hours. The membrane was blocked with 10 mmol/L Tris, 150 mmol/L NaCl, pH 7.6 with 1% Tween 20 TBST) and 5% bovine serum albumin at room temperature for one hour, washed three times with TBST, and then incubated with the primary antibody diluted to 1 ug/ml in TBST for one hour. The membrane was washed three times, incubated for one hour with the appropriate horseradish peroxidase-linked secondary antibody diluted 1:10,000 in TBST and then washed three times. Detection by enhanced chemiluminescence was performed according to the manufacturer's specifications (Amersham, Arlington Heights, Ill.). Membranes were reprobed with different anubodies after stripping in 62.5 mmol/L Tris, pH 6.7 with 2% SDS and 100 mmol/L 2-mercaptoethanol at 70° C. for 30 minutes. For immunoprecipitation, antibody was added to the platelet lysate (200 µg lysate diluted to 1 µg/µl in lysis buffer) at a concentration of 1 µg/0.1 ml and incubated at 4° C. for 2 hours. Protein A Sepharose (0.1 ml of a 50% slurry in lysis buffer) was added to the lysate and incubated for an additional hour at 4° C. with rocking. The sample was then washed 4 times with 10 mM Tris pH 7.4 with 1% Triton X-100, 150 mM NaCl, 1 mM EGTA, 2 mM sodium vanadate and 1 mM PMSF, resuspended in SDS-PAGE sample buffer, boiled for 5 minutes, and subjected to SDS-PAGE and transfer to nitrocellulose for immunoblotting as described above.

Reagents. The antiphosphotyrosine antibody PY20 and STAT5 antiserum were purchased from Santa Cruz Biotechnology (Santa Cruz, Calif.). The JAK2 antiserum was purchased from Upstate Biotechnology Incorporated (Lake Placid, N.Y.). Full length TPO was purchased from R & D Systems Incorporated (Minneapolis, Minn.). Bovine thrombin was purchased from Armour Pharmaceutical Company.

Example 2

This example describes JAK2 autophosphorylation.

Figure 2:
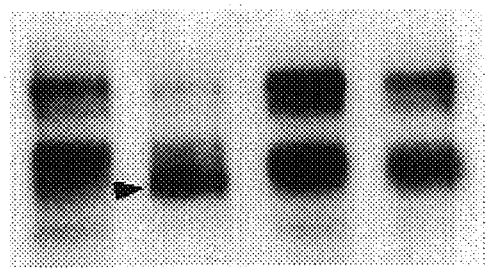
FIG. 2. TPO-induced JAK2 kinase activity. Jak2 immunoprecipitates from normal (1,2) and PV(3,4) platelet lysates unstimulated (1,3) or after TPO stimulation (100 ng/ml for 10 minutes) lanes 2 and 4) were subsequently incubated with [γ-$^{32}$P]ATP, then subjected to SDS-PAGE and autoradiography. The upper panel demonstrates the increase in autophosphorylation in normal platelets (arrow) after TPO exposure which was not present in the PV platelets. The membrane was reprobed with JAK2 antiserum to demonstrate equivalent amounts of JAK2 in the samples.
Figure 2:
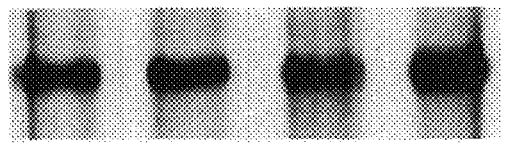

To examine further the abnormalities in TPO-induced platelet protein tyrosine phosphorylation, we employed an immunokinase assay to assess the enzymatic behavior of JAK2. As shown in FIG. 2, TPO stimulation of normal platelets resulted in the autophosphorylation of JAK2 as assessed by $^{32}$P-ATP incorporation. However, in the case of PV platelets, TPO stimulation failed to produce the same effect.

Example 3

This example describes expression of Mpl in normal and PV platelets.

Figure 3A:
FIG. 3A) Immunoblot of platelet lysates from normal (lane 1) and four different PV patients (lanes 2–5) with Mpl antiserum. The membrane was stripped and reprobed with GPIIIa antiserum (lower panel) to demonstrate equal platelet protein loading.
Figure 3B:
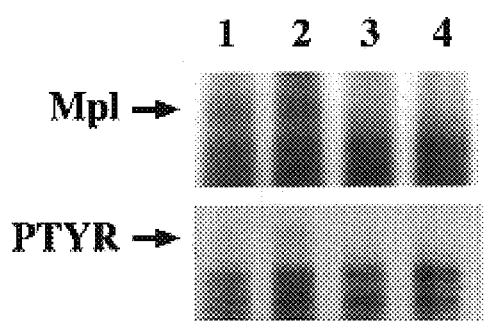
FIG. 3B) Mpl immunoprecipitates from normal (1,2) and PV(3,4) platelet lysates before (1,3) and after TPO stimulation (2,4) probed with antiphosphotyrosine antiserum (upper panel) and Mpl antiserum (lower panel).

The abnormalities in PV platelet protein tyrosine phosphorylation and JAK2 autophosphorylation described above could be a consequence of an abnormality in either JAK2 or Mpl. Since the concentration and electrophoretic mobility of JAK2 appeared normal in PV platelets, we next examined the expression of platelet Mpl by immunoblotting using an antibody to the extacellular domain. As shown in FIG. 3A, for equal quantities of platelet lysate protein, Mpl expression was markedly reduced in PV platelets as compared to normal controls. Immunoprecipitation experiments also demonstrated that Mpl present in normal platelets became tyrosine phosphorylated after TPO stimulation (FIG. 3B). Similar experiments in PV platelets failed to induce tyrosine phosphorylation of a protein of the appropriate molecular weight of Mpl.

Figure 4:
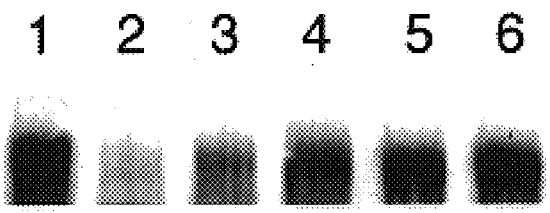
FIG. 4. Mpl immunoblot of normal or PV platelet lysates following incubation in normal plasma, PV plasma or exogenous 1TPO. (1) Normal platelets; (2) PV platelets; (3) equal numbers of PV and normal platelets mixed prior to lysis; (4) normal platelets incubated with TPO (100 ng/ml at 37° C. overnight) before lysis; (5) normal platelets incubated in normal plasma at room temperature overnight before lysis; (6) normal platelets incubated in PV plasma at room temperature overnight before lysis.
Figure 5A:
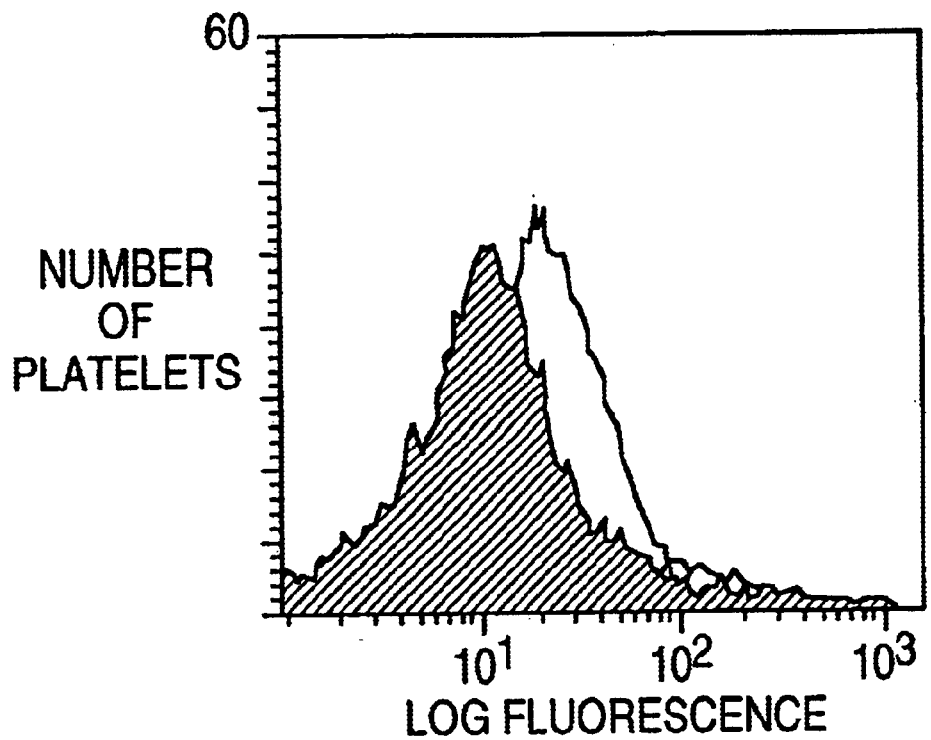
FIG. 5. Flow cytometric analysis of platelet surface Mpl expression. The upper panel is the study from a control subject, the lower panel is a study from a PV patient. The solid curve represents fluorescence due to binding of a nonspecific rabbit IgG; the open curve represents fluorescence due to the binding of the Mpl antiserum.
Figure 5B:
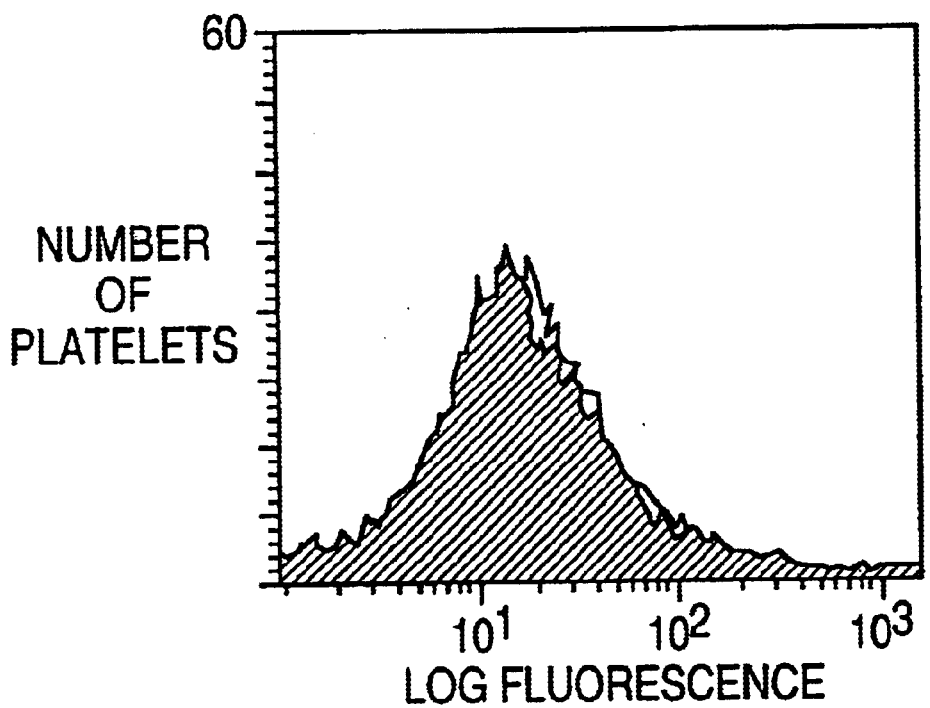
Figure 6A:
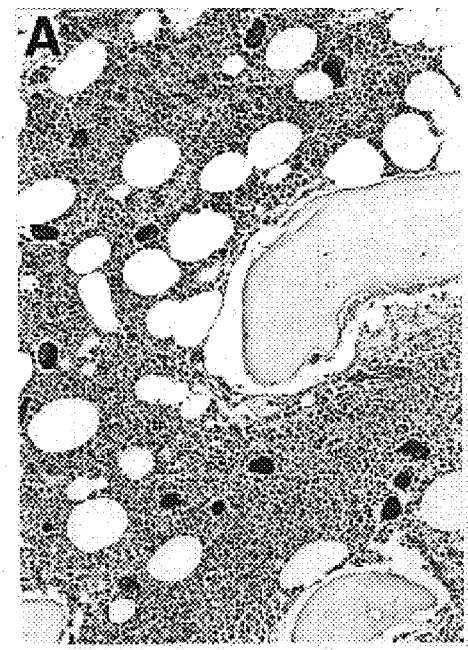
FIG. 6. Immunohistochemical staining of bone marrow biopsies with Factor VIII antiserum (panels A and B) or Mpl antiserum (panels C and D) in an ET patient (A and C) and a PV patient B3 and D).
Figure 6B:
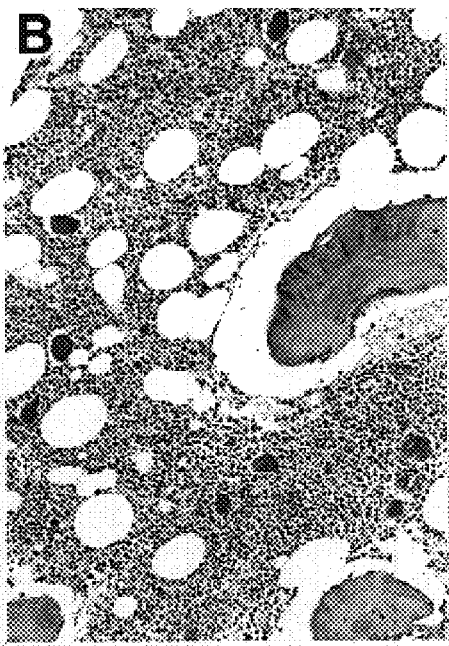
Figure 6C:
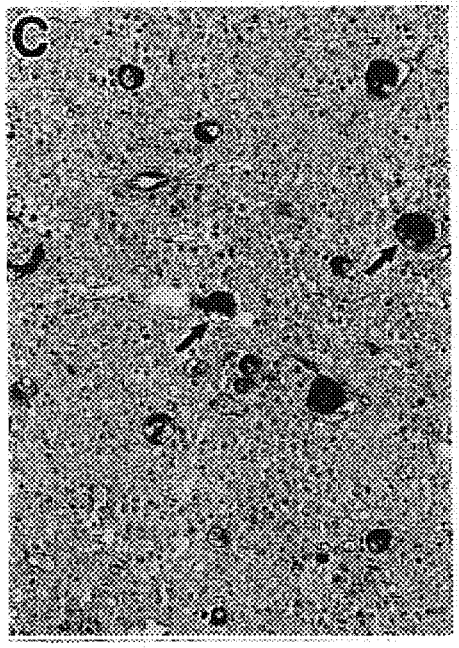
Figure 6D:
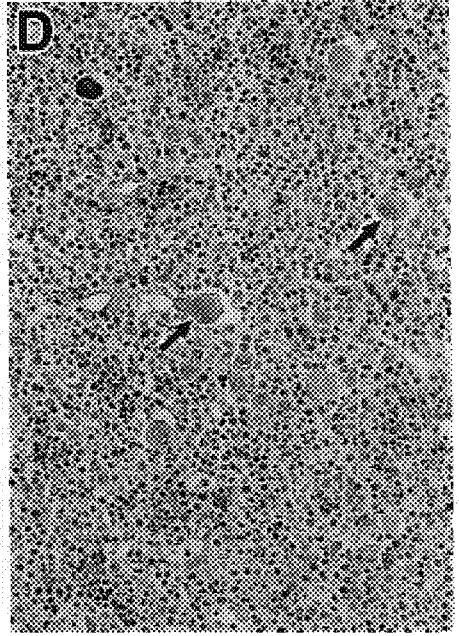
Figure 7:
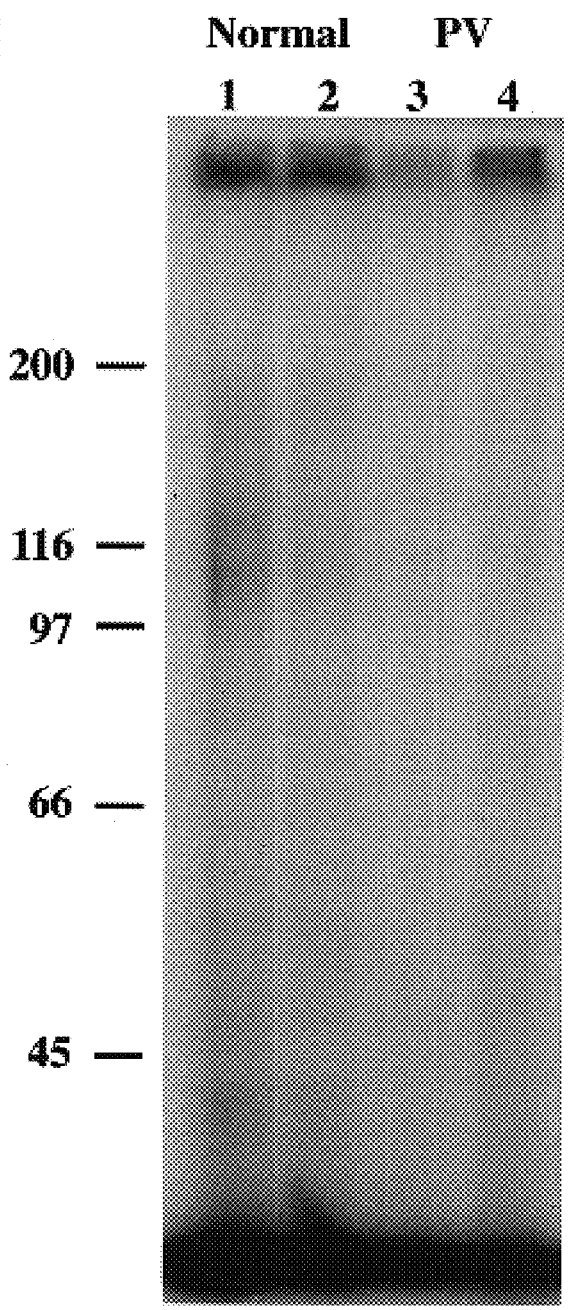
FIG. 7. Crosslinking of $^{125}$I-TPO to normal or PV platelets. Normal (lanes 1,2) or PV lanes 3,4) platelets were incubated with 2 ng of $^{125}$I-labeled, full length recombinant TPO in the absence (lanes 1 and 3) or presence (lanes 2 and 4) of a 100 -fold excess of unlabeled TPO for 2.5 hours at room temperature, washed and then exposed to 500 uM DSS for 30 minutes at room temperature. The reaction was quenched and the platelets lysed and subjected to SDS-7.5% PAGE and autoradiography for 12 days.

To ensure that impaired PV platelet Mpl expression was not a consequence of proteolysis during platelet isolation, or down regulation by TPO or by as yet undefined agents present in PV plasma, we examined platelet Mpl expression using lysates prepared from a mixture of equal quantities of normal and PV platelets, following incubation of normal platelets in PV plasma or after prolonged exposure of normal platelets to a saturating concentration of TPO. In no instance was Mpl expression in normal platelets impaired by these manipulations (FIG. 4). Additionally, diminished PV platelet Mpl was also confirmed using freshly isolated platelets analyzed with flow cytometry, excluding ex vivo manipulation as a cause of this defect (FIG. 5). These results suggested that the abnormalities in TPO-induced platelet protein tyrosine phosphorylation, specifically in JAK2 phosphorylation and enzymatic activation and STAT5 tyrosine phosphorylation, were likely the result of aberrant Mpl expression, as opposed to inherent defects in JAK2 or STAT5.

Platelet Flow Cytometry. Platelet-rich plasma prepared as described above was incubated with non-specific rabbit IgG or Mpl antiserum for 30 minutes at 4° C., washed once, exposed to a FITC-labeled sheep anti-rabbit (Boerhinger-Mannheim, Indianapolis) for 30 minutes at 4° C. and washed again. 10,000 labeled platelets were analyzed with a FACSCAN Becton-Dickinson, San Jose ) flow cytometer. Reagents. Affinity-purified, polyclonal rabbit IgG to the soluble extracellular domain of human Mpl was a gift from Kirin Brewery Company Limited (Maebashi Gunma, Japan).

Example 4

This example describes chemical crosslinking of radiolabeled TPO to normal or PV platelets.

The studies described above indicated that Mpl expression was impaired in PV platelets whether assessed by immunoblotting or flow cytometry using an anti-extracellular domain of Mpl antibody. To determine if PV platelets were able to bind TPO, we employed chemical crosslinking following exposure to radiolabeled TPO. As shown in FIG. 4, incubation of normal platelets with biologically active $^{125}$I-TPO(45 kd) and subsequent exposure to the chemical crosslinker disuccinimidyl suberate (DSS) yielded several bands on autoradiography, the most prominent of which corresponded to a molecular weight of 130 kd, which is compatible with a monomeric TPO-Mpl complex. However, the same experiment performed with PV platelets failed to yield the expected crosslinked receptor-ligand complexes.

Example 5

This example describes platelet aggregation.

Previous studies have demonstrated that TPO enhances thrombin mediated platelet aggregation (13). Therefore, whole blood aggregometry was employed to determine if PV platelets could respond functionally to TPO. As shown in FIG. 5, preincubation of normal blood with TPO (100 ng/ml for 2 minutes) resulted in enhanced aggregation in response to 0.1 unit/ml thrombin as compared to the response to thrombin in the absence of TPO. However, preincubation with TPO did not enhance PV platelet aggregation in response to thrombin, which was in keeping with the impaired PV platelet Mpl expression documented above.

Example 6

This example describes plasma TPO levels in PV patients.

Previous studies have established an inverse correlation between megakaryocyte and platelet mass and plasma TPO levels, presumably due to downregulation of TPO by receptor-ligand interactions (17,18). We therefore measured plasma TPO levels in PV patients and normal subjects. As shown in FIG. 6, the mean plasma TPO concentration was significantly higher (p<0.05) in PV patients (407 pg/ml) and IMF patients (292 pg/ml) than in normal individuals (133 pg/ml). There was no correlation, however, in the PV patients between the platelet count and the plasma TPO level (data not shown). The elevated TPO levels in the PV and IMF patients support the notion that Mpl-mediated clearance of TPO is compromised in these patients.

Plasma TPO Assay. TPO was measured in EDTA-anticoagulated plasma samples from patients and controls using an enzyme-linked immunoassay supplied by Amgen (Thousand Oaks, Calif.).

Example 7

This example describes reduced platelet Mpl is specific for PV and The.

To assess the specificity of impaired platelet Mpl expression, we examined platelet Mpl expression by immunoblotting and densitometry in 34 patients with PV, 14 patients with IMF, 9 patients with ET, 7 patients with CML, 14 patients with secondary or undefined erythrocytosis, 8 patients with hemochromatosis undergoing periodic therapeutic phlebotomy, 2 patients with uncomplicated iron deficiency and 10 normal volunteers. All 34 PV patients had decreased Mpl expression (defined as less than 40% of control Mpl as determined from densitometric analysis of immunoblots) in contrast to the patients with ET, CML, erythrocytosis, hemochromatosis, iron deficiency and the normal volunteers. There was no correlation between decreased Mpl expression in PV platelets and the platelet count, hemoglobin level, leukocyte count, disease duration, spleen presence or size, iron deficiency, aspirin use or concurrent hydroxyurea or alpha-interferon therapy. Interestingly, platelet Mpl expression was also decreased in 13 of the 14 IMF patients studied. The concordance for decreased TPO-induced protein tyrosine phosphorylation and decreased Mpl expression was absolute in the 18 patients (16 PV and 2 IMP) where the platelet sample was sufficient to assay both Densitometric analysis. Autoradiographs of immunoblots were scanned with a HP ScanJet IIc and densitometry was performed with NIH Image software (version 2.3). Absorbance of the 85-kDa band, Mpl, was quantified as the area under the peak for the band and expressed in arbitrary units. Pilot experiments defined the amount of platelet lysate protein (35 ug) which produced a linear response. Protein loading was controlled by reprobing the membrane with glycoprotein IIIa antisera to authenticate that equal amounts of platelet lysate were present (FIG. 4). Percentage of Mpl expression was determined by dividing the patient absorbance units by the average absorbance units of the control subjects on the same immunoblot. The variance among control subjects on a given immunoblot was never more than 15%.

Example 8

This example describes megakaryocyte Mpl expression.

Figure 8:
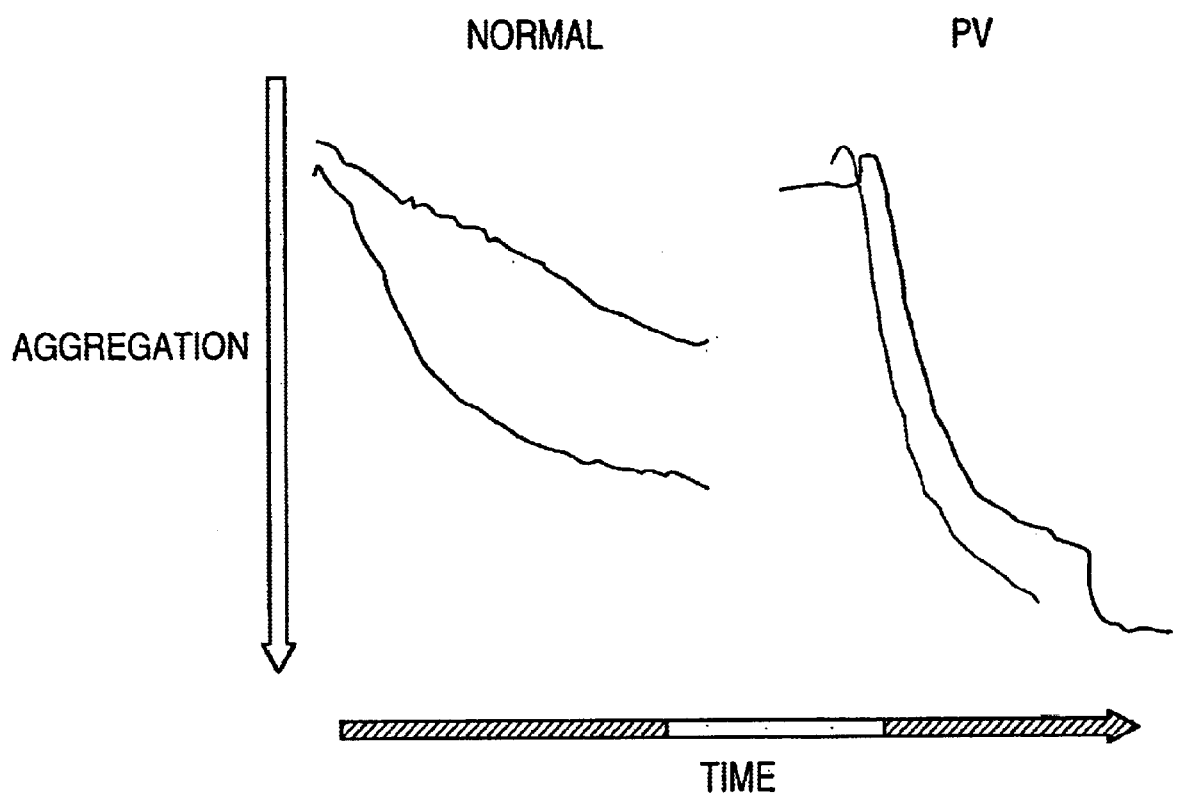
FIG. 8. Whole blood aggregometry in normal and PV platelets. Gray lines indicate aggregation in response to 0.1 U/ml thrombin, black lines indicate aggregation in response to thrombin after preincubation with TPO (100 ng/ml for one minute) in a normal subject (left panel) and a PV patient (right panel).
Figure 9:
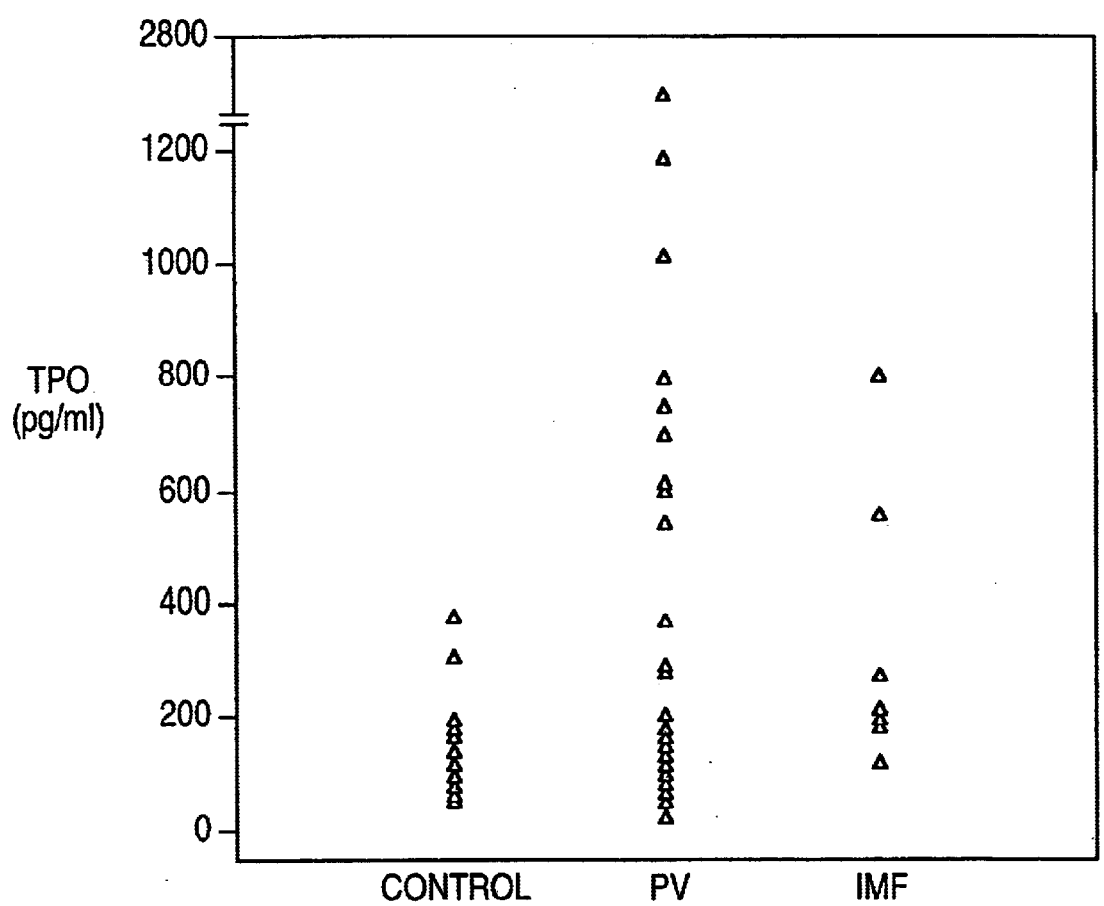
FIG. 9. Plasma TPO levels in normal, PV and IMF patients. TPO was measured in EDTA-anticoagulated plasma samples from patients and controls with an enzyme-linked immunoassay (21).

To determine if Mpl expression was reduced in PV megakaryocytes as well as PV platelets, bone marrow biopsy specimens were examined by immunohistochemical staining with Mpl antiserum. As shown in FIG. 8, as compared to the control, Mpl protein expression was markedly reduced in the PV megakaryocytes.

Immunohistochemistry of Bone Marrow Biopsies. Sequential bone marrow biopsy sections from PV patients or control subjects were exposed to either the affinity-purified rabbit Mpl antiserum at a dilution of 1:300 or goat anti-human Factor VIII antisera (Dako, Carpenteria, Calif.) at a dilution of 1:100 followed by exposure to the appropriate peroxidase-labeled secondary antibody and substrate.

References

1. Adamson J W, Fialkow P J, Murphy S, Prchal J F, Steinmann L. Polycythemia vera: stem-cell and probable clonal origin of the disease. N Engi J Med 1976;295:913–916.
2. Jacobson R J, Sao A, Fialkow P J. Agnogenic myeloid metaplasia: a clonal proliferation of hematopoietic stem cells with secondary myelofibrosis. Blood 1978;51:189–194.
3. Fialkow P J, Jacobson R J, Singer J W, Sacher R A, McGuffin R W, Neefe J R. Philadelphia chromosome (Ph1)-negative chronic myelogenous leukemia (CML): a clonal disease with origin in a multipotent stem cell. Blood 1980;56:70–73.
4. Fialkow P J, Faguet G B, Jacobson R J, Vaidya K, Murphy S. Evidence that essential ttirombocythemia is a clonal disorder with origin in a multipotent stem cell. Blood 1981;58:916–919.
5. Marsh J C W, Gibson F M, Prue R L et al. Serum thrombopoietin levels in patients with aplastic anemia. Br J Haematol 1996;95;605–610.
6. Vignon I, Mornon J P, Cocault L et al. Molecular cloning and characterization of MPL, the human homolog of the v-mpl oncogene: identification of a member of the hematopoietic growth factor receptor superfamily. Proc Natl Acad Sci USA 1992;89:5640–5644.
7. Mignotte V, Vigon I, Crevecoeur E et al. Structure and transcription of the human c-mpl gene (MPL). Genornics 1994;20:5–12.
8. Hoffman R and Boswell H S. Poycythemia Vera in Hoffinan R, Benz E J Jr, Shattil S J et al.,eds. Hematology. New York: Churchill Livingstone pp 1121–1142, 1995.
9. Means R T, Krantz S B, Sawyer S T, Gilbert H S. Erythropoietin receptors in polycythemia vera. J Clin Invest 1989;84: 1340–1344.
10. Hess G, Rose P, Gammn H Papadileris S, Huber C, Seliger B. Molecular analysis of the erythropoietin receptor system in patients with polycythaemia vera. Br J Haematol 88:794–802, 1994.
11. Emanuel P D, Eaves C J, Broudy V C, et al. Familial and congenital polycythemia in three unrelated families. Blood 1992;79:3019–3030.
12. Drachman J G, Griffin J D, Kaushansky K. The c-Mpl ligand (thrombopoietin) stimulates tyrosine phosphorylation of JAK2, Shc, and c-Mpl. J Biol Chem 1995;270:49794982.
13. Ezumi, Y, Takayama H. Okuma M. Thrombopoietin, c-Mpl ligand, induces tyrosine phosphorylation of Tyk2, JAK2, and STAT3, and enhances agonists-induced aggregation in platelets in vitro. FEBS Letters 1995;374:48.
14. Cooper B, Ahern D. Characterization of the platelet prostaglandin D2 receptor. Loss of prostaglandin D2 receptors in platelets of patients with myeloproliferative disorders. J Curn Invest 1979;64:586–590.
15. Kaywin P, McDonough M, Insel PA et al. Platelet function in essential thrombocythemia. Decreased epinephrine responsiveness associated with a deficiency of platelet alpha-adrenergic receptors. N Engl J Med 1978;299:505–509.
16. Berk P D, Goldberg J D, Donovan P B et al. Therapeutic recommendations in polycythemia vera based on polycythemia vera study group protocols. Semin Hematol 1986;23:132–143.
17. Kuter D J, Rosebberg R D. The reciprocal relationship of thrombopoietin (c-Mpl ligand) to changes in the platelet mass during busulfan-induced thrombocytopenia in the rabbit. Blood 1995;85:2720–2730.
18. Emmons R V B, Reid D M, Cohen R L, et al. Human thrombopoietin levels are high when thrombocytopenia is due to megakaryocyte deficiency and low when due to increased platelet destruction. Blood 1996;87:4068–71.

What is claimed is:

1. An antibody preparation which specifically binds to the cytoplasmic domain of Mpl protein and does not specifically bind to the extracellular domain of Mpl.

2. The antibody preparation of claim 1 which is polyclonal.

3. The antibody preparation of claim 1 which is monoclonal.

* * * * *

UNITED STATES PATENT AND TRADEMARK OFFICE
CERTIFICATE OF CORRECTION

PATENT NO. : 6,696,549 B1
DATED : February 24, 2004
INVENTOR(S) : Jerry Spivak et al.

It is certified that error appears in the above-identified patent and that said Letters Patent is hereby corrected as shown below:

Title page,
Item [56], References Cited, insert the following:
-- U.S. PATENT DOCUMENTS

| | | | |
|---|---|---|---|
| 5,427,913 | 6/1995 | Shaw Andrew | 435/7.21 |
| 5,656,442 | 8/1997 | Ginsberg | 435/7.21 |
| 5,728,536 | 3/1998 | Ihle | 435/7.21 |
| 6,027,902 | 2/2000 | Spivak | 435/7.1 |

FOREIGN PATENT DOCUMENTS

| | | |
|---|---|---|
| 92 07074 | 4/1992 | WIPO -- |

Signed and Sealed this

Seventeenth Day of May, 2005

JON W. DUDAS
*Director of the United States Patent and Trademark Office*